United States Patent
Fukatsu et al.

(10) Patent No.: US 9,280,818 B2
(45) Date of Patent: Mar. 8, 2016

(54) MEDICAL REPORT WRITING SUPPORT SYSTEM, MEDICAL REPORT WRITING UNIT, AND MEDICAL IMAGE OBSERVATION UNIT

(71) Applicant: Toshiba Medical Systems Corporation, Otawara-shi (JP)

(72) Inventors: Hiroshi Fukatsu, Nagoya (JP); Koichi Terai, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/802,301

(22) Filed: Jul. 17, 2015

(65) Prior Publication Data

US 2015/0324980 A1 Nov. 12, 2015

Related U.S. Application Data

(63) Continuation of application No. 13/849,159, filed on Mar. 22, 2013, now abandoned, which is a continuation of application No. 13/569,611, filed on Aug. 8, 2012, now abandoned.

(30) Foreign Application Priority Data

Aug. 8, 2011 (JP) .................................. 2011-173448

(51) Int. Cl.
*G06K 9/00* (2006.01)
*G06T 7/00* (2006.01)
(Continued)

(52) U.S. Cl.
CPC .......... *G06T 7/0012* (2013.01); *G06F 19/3487* (2013.01); *G06K 9/6202* (2013.01); *G06T 2207/10004* (2013.01)

(58) Field of Classification Search
USPC ......... 382/100, 128–134, 155, 168, 176, 181, 382/186–191, 209, 219, 224, 232, 254, 382/274–276, 305, 312, 294; 345/619; 705/2, 3

See application file for complete search history.

(56) References Cited

U.S. PATENT DOCUMENTS

| 7,607,079 B2 * | 10/2009 | Reiner | G06F 3/04883 345/619 |
| 7,978,890 B2 * | 7/2011 | Yamagishi | G06F 19/321 382/128 |

(Continued)

FOREIGN PATENT DOCUMENTS

| JP | 2002-229835 | 8/2002 |
| JP | 2004-334466 | 11/2004 |

(Continued)

OTHER PUBLICATIONS

Office Action issued Mar. 10, 2015 in Chinese Patent Application No. 201210279979.1.

(Continued)

*Primary Examiner* — Seyed Azarian
(74) *Attorney, Agent, or Firm* — Oblon, McClelland, Maier & Neustadt, L.L.P.

(57) ABSTRACT

According to one embodiment, a medical report writing support system comprises an analyzing unit which analyzes a difference regarding at least one of a change in key images between a first report and a second report regarding a predetermined patient and a change in hyperlinks, and acquires an analyzed result, and a difference information generation unit which generates difference information based on the analyzed result.

15 Claims, 10 Drawing Sheets

(51) Int. Cl.
*G06K 9/62* (2006.01)
*G06F 19/00* (2011.01)
*G06Q 10/00* (2012.01)

(56) References Cited

U.S. PATENT DOCUMENTS

| | | | |
|---|---|---|---|
| 8,751,267 B2* | 6/2014 | Kurosawa | G06F 19/321 382/128 |
| 2007/0237378 A1 | 10/2007 | Reiner | |
| 2011/0153351 A1* | 6/2011 | Vesper | G06Q 10/10 705/2 |
| 2011/0320218 A1* | 12/2011 | Kurosawa | G06Q 50/24 705/3 |

FOREIGN PATENT DOCUMENTS

| | | |
|---|---|---|
| JP | 2005-18433 | 1/2005 |
| JP | 2005-301453 | 10/2005 |
| JP | 2010-204993 | 9/2010 |
| JP | 2011-125402 | 6/2011 |

OTHER PUBLICATIONS

Office Action issued Mar. 10, 2015 in Japanese Patent Application No. 2011-173448.

* cited by examiner

Found small amount of right pleural effusion
Not found ~~specific~~ enlarge lymph node in chest

FIG. 8

~~Found amount of right pleural effusion~~
Found small amount of right pleural effusion
~~Not found specific enlarge lymph node in chest~~
Not found enlarge lymph node in chest

FIG. 9

| Observation | Before correction | Latest version | Differential display |

~~Found amount of right pleural effusion~~
Found small amount of right pleural effusion
~~Not found specific enlarge lymph node in chest~~
Not found enlarge lymph node in chest

FIG. 10

MEDICAL REPORT WRITING SUPPORT SYSTEM, MEDICAL REPORT WRITING UNIT, AND MEDICAL IMAGE OBSERVATION UNIT

CROSS-REFERENCE TO RELATED APPLICATIONS

This application is a continuation of and claims the benefit of priority under 35 U.S.C. §120 from U.S. Ser. No. 13/849,159 filed Mar. 22, 2013, which is a continuation of U.S. application Ser. No. 13/569,611 filed Aug. 8, 2012, and claims the benefit of priority under 35 U.S.C. §119 from Japanese Patent Application No. 2011-173448 filed Aug. 8, 2011, the entire contents of each of which are incorporated herein by reference.

FIELD

Embodiments described herein relate generally to a medical report writing support system, a medical report writing unit, and a medical image observation unit.

BACKGROUND

In recent years, specialization of medical practice is subdivided. For example, image diagnosis includes several different works that are: acquisition of a diagnostic image for a patient; (radiological) interpretation of the acquired diagnostic image and writing a report for it; and explanation of a diagnostic result and medical practice plan, based on a result of the report. Each of the works is taken under each specialist's charge (attending doctor or attending engineer or technician). All these works are done to achieve the medical practice for the diagnosis of a corresponding patient. Each of the specialists executes each medical work by referring to appropriate past diagnostic information, and based on information written by another specialist during the medical work of the previous stage. These medical works are performed using, for example, an X-ray CT system acquiring diagnostic images, a medical image pickup unit (MRI system), a medical image storage unit (PACS server) storing the diagnostic images, and a medical image observation unit for an (radiological) interpretation on the diagnostic images.

That is, first of all, a requested doctor (attending doctor) forms an examination (study) order (a request for examination to be done next and which is transmitted to various medical image pickup unit through a network N using an order system), based on an inquiry for each patient, and informs a laboratory technician about it. Then, the informed laboratory technician performs an examination using a predetermined medical image pickup unit, and acquires a medical image about a corresponding patient. A radiologist uses a medical report writing unit to write a radiological report corresponding to the examination order. The requested doctor refers to the written report, decides a result of image diagnosis, performs diagnosis on the image in combination with another information, and then performs medical practice for the patient.

In the medical report writing unit in the recent years, a plurality of operators can write a medical report. For example, a young radiologist (primary operator) first performs an interpretation, writes a temporary storage report. Then, an expert radiologist (secondary operator) checks and corrects the contents of this report as needed, and finally stores the report. The corrected contents, which are made by the secondary operator on the temporarily stored report, can be said as effective information especially for the primary operator or other operators who have referred to the temporarily stored report.

However, the existing medical report writing units do not include a system which certainly and clearly notifies the corrected contents to the participant operators.

BRIEF DESCRIPTION OF THE DRAWINGS

FIG. 8 is a diagram illustrating an example of a form showing a change in text strings, according to the embodiment;

FIG. 9 is a diagram illustrating another example of a form showing changes in text strings, according to the embodiment;

FIG. 10 is a diagram illustrating an example of a screen of a display unit showing changes in text strings, according to the embodiment;

DETAILED DESCRIPTION

Figure 1:
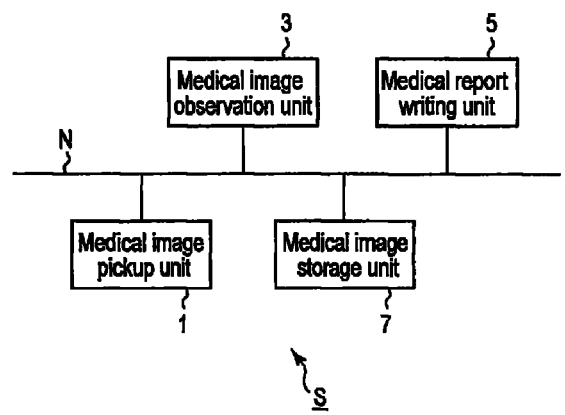
FIG. 1 is a diagram for explaining a configuration of a medical image diagnostic system according to an embodiment.

In general, according to one embodiment, a medical report writing support system comprises an analyzing unit which analyzes a difference regarding at least one of a change in key images between a first report and a second report regarding a predetermined patient and a change in hyperlinks, and acquires an analyzed result; and a difference information generation unit which generates difference information based on the analyzed result.

Embodiment will now specifically be described with reference to the drawings. In the following descriptions, the same functions and configurations are identified with the same reference numerals, and will repeatedly be described again only if needed.

First Embodiment

FIG. 1 is a diagram for explaining a configuration of a medical image diagnostic system S according to this embodiment. As illustrated in FIG. 1, the medical image diagnostic system S includes a medical image pickup unit 1, a medical image observation unit 3, a medical report writing unit 5, and a medical image storage unit 7. These units are connected with each other through a network N, and can transmit data with each other. Configurations of these units will be described below.

[Medical Image Pickup Unit]

The medical image pickup unit 1 is used for collecting images in accordance with an order made by an attending doctor, and may be any of various units, of: an X-ray computer tomographic pickup unit; a magnetic resonance imaging unit; an X-ray diagnostic unit; a nuclear medical diagnostic unit; and an ultrasonic diagnostic unit. The medical image pickup unit 1 is not limited to including these kinds of units. Images picked up by this medical image pickup unit 1 are transmitted to the medical image storage unit 7 in DICOM format.

[Medical Image Observation Unit]

The medical image observation unit 3 displays the medical images, and is used when a user writes and edits or refers to a medical report. Note that the medical image observation unit 3 and the medical report writing unit may physically be incorporated in one unit.

Figure 2:
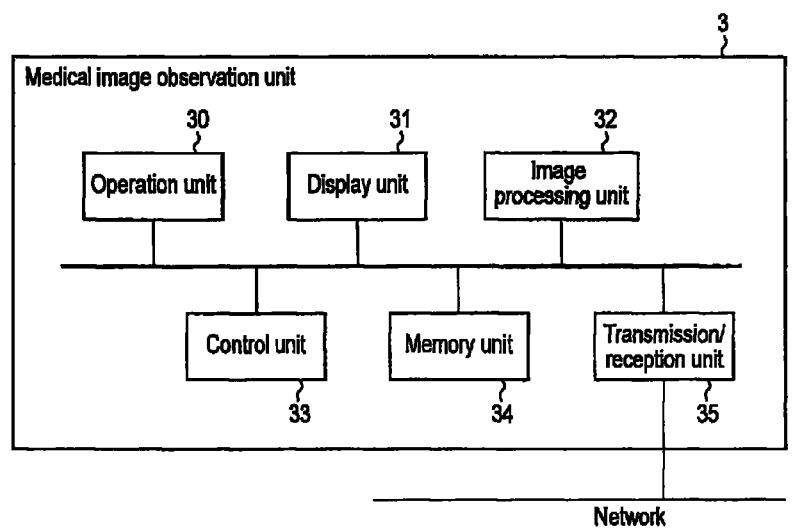
FIG. 2 is a diagram illustrating a block configuration of a medical image observation unit according to the embodiment.

FIG. 2 is a diagram illustrating a block configuration of the medical image observation unit 3. As illustrated, the medical image observation unit 3 includes an operation unit 30, a display unit 31, an image processing unit 32, a control unit 33, a memory unit 34, and a transmission/reception unit 35.

The operation unit 30 includes a keyboard, various switches, a mouse, and a button (for example, GUI), and can input instructions (various instructions including: display, gradation change, enlargement/reduction, adding/deleting/changing of annotation) from the operator. The operation unit 30 has an I/F for instructing execution of the medical report writing support process, as will be described later.

The display unit 31 displays an image which has been processed in accordance with a predetermined image process by the image processing unit 32, in a predetermined form.

The image processing unit 32 performs a predetermined image process, such as volume rendering, surface rendering, MPR (multi planar reconstruction), and MIP (maximum intensity projection).

The control unit 33 controls an overall static or dynamic operation of the medical image observation unit 3. The control unit 33 develops a dedicated program into a non-illustrative memory, thereby enabling to realize the medical report writing support process, as will be described later.

The memory unit 34 stores various medical images (for example, images based on the DICOM standard) acquired by the medical image pickup unit 1 or medical images which have been processed in accordance with a predetermined image process in the medical image observation unit 3. The medical images are managed based on various management information, such as the examination (study), series, patient, and doctor, as needed.

The transmission/reception unit 35 receives a medical image as a target object to be observed through the network N and various information necessary for writing/editing a medical report, from the medical image pickup unit 1. The transmission/reception unit 35 transmits a medical image which has been processed in accordance with the image process by the image processing unit 32, to the medical image storage unit 7 through the network N.

[Medical Report Writing Unit 5]

The medical report writing unit 5 is used for writing/editing a report, recording the doctor's observation through the image diagnosis. The user refers to the medical image displayed on the medical image observation unit 3, and inputs a comment on a medical report writing screen of the medical report writing unit 5, thereby writing and editing a medical report.

Figure 3:
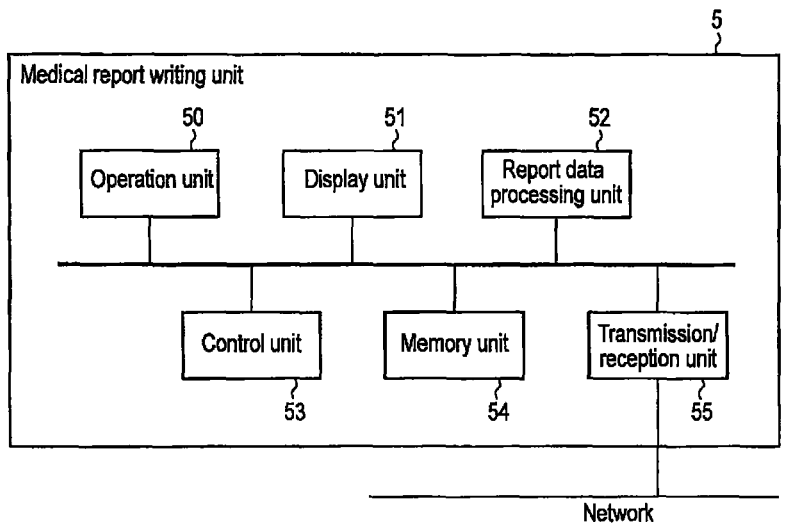
FIG. 3 is a block diagram for explaining a configuration of a medical report writing unit according to the embodiment.

FIG. 3 is a block diagram for explaining a configuration of the medical report writing unit 5. As illustrated, the medical report writing unit 5 includes an operation unit 50, a display unit 51, a report data processing unit 52, a control unit 53, a memory unit 54, and a transmission/reception unit 55.

The operation unit 50 includes a keyboard, various switches, and a mouse, and is a unit for the operator to input an instruction for displaying a medical report about examination and a key input for operating the report writing screen.

The display unit 51 displays an image acquired by the medical image pickup unit 1, the report which is written on the report writing/editing screen and by the report writing unit 5, the past report received from the medical image storage unit 7, difference information acquired in the medical report writing support process as will be described later, in a predetermined form.

The report data processing unit 52 writes and edits medical reports in accordance with an input from the operation unit 50. Note that editing of the medical report implies adding, deleting, and changing of a key image (image as a reason or base of the diagnosis), comment, and hyperlink, included in the medical report.

The control unit 53 controls an overall operation of the medical report writing unit 5. Particularly, the control unit 53 develops a dedicated program into a non-illustrative memory, thereby executing the medical report writing support process, as will be described later.

The memory unit 54 stores the previously written report and a report as a presently written backup report. The memory unit 54 stores a dedicated program for realizing the medical report writing support system, as will be described later.

The transmission/reception unit 55 receives various information for writing/editing a target past medical report and present medical report, to be edited through the network. The transmission/reception unit 55 transmits the report written/edited by the report data processing unit 52 to the medical image storage unit 7, through the network.

[Medical Image Storage Unit]

The medical image storage unit 7 stores images collected by the medical image pickup unit 1, registers, manages, and stores the images on the management information, such as a database. The medical image storage unit 7 stores the medical report written by the medical report writing unit 5, and manages the report in accordance with the management information. Further, the medical image storage unit 7 performs difference analysis and generates difference information, in the medical report writing support process, as will be described later.

Figure 4:
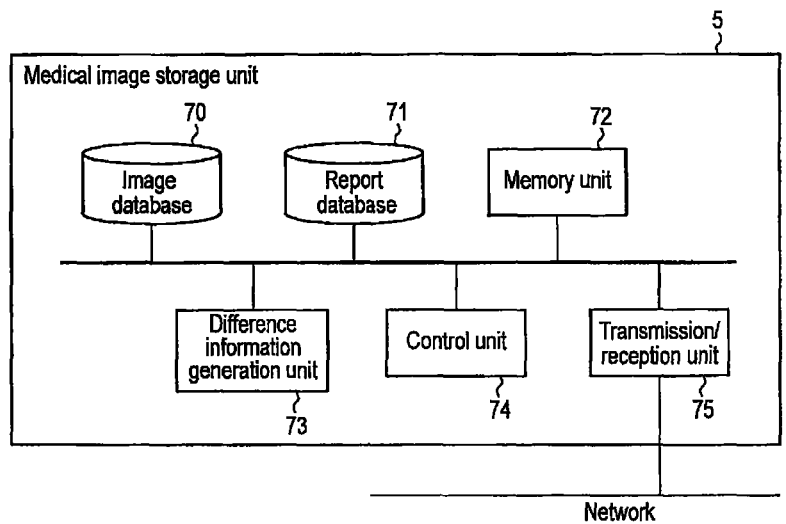
FIG. 4 is a block diagram for explaining a configuration of a medical image storage unit according to the embodiment.

FIG. 4 is a block diagram for explaining a configuration of the medical image storage unit 7. As illustrated, the medical image storage unit 7 includes an image database 70, a report database 71, a memory unit 72, a difference information generation unit 73, a control unit 74, and a transmission/reception unit 75.

The image database 70 receives an image acquired by the medical image pickup unit 1 and an image which has been processed in accordance with an image process in the medical image observation unit 3, through the network N, and stores and manages the images based on the management information.

The report database 71 receives the medical report written/edited by the medical report writing unit 5 through the network N, stores and manages the received report based on predetermined attributes (operator, patient, examination type). The medical report has a "version number" as a concept representing the sequential revised order, such as "first version" or "second version" (that is, the smaller the version number, the older (past in time) the report is, and the larger the version number, the newer the report is). The corresponding report database 71 manages information of the entire versions of the medical report.

The memory unit 72 stores a dedicated program for realizing the medical report writing support process, as will be described later.

The difference information generation unit 73 compares the latest medical report data to be received after notification of completion of operation with report data of earlier version (past version) which is stored in the report DB, and analyzes difference information. For example, the difference information generation unit 73 analyzes a difference between text strings of the medical report, between key images attached to the medical report, and between hyperlinks attached to the text string of the medical report.

The control unit 74 controls an overall operation of the medical image storage unit 7. The control unit 74 searches for an image stored in the image database 70 and a medical report stored in the report database 71, based on the management information. Further, the control unit 74 develops a dedicated program into a non-illustrative memory, thereby realizing report writing/editing application and the medical report writing support process, as will be described later.

The transmission/reception unit 75 transmits interpretation diagnosis, information necessary for writing a medical report, a past report, and a past medical image, to the medical image observation unit 3 and the medical report writing unit 5 through the network N, as needed.

(Medical Report Writing Support System)

Descriptions will now be made to the medical report writing support system. When a plurality of operators write and edit the medical report, this medical report writing support system analyzes a difference between a predetermined report and a report with a smaller version number (old in time) than that of the predetermined report, generates difference information to obviously notify operators about the difference.

In this embodiment, for concrete descriptions, for example, it is assumed that an expert radiologist as a secondary operator edits the contents of a temporarily stored report, which has been written by a young radiologist as a primary operator. In this case, the medical report written by the secondary operator through an editing process is compared with the medical report written by the primary operator. Analysis is made on a difference between the two medical reports. When a difference exists between the two medical reports, difference information is generated and informed to the participant operators.

Figure 5:
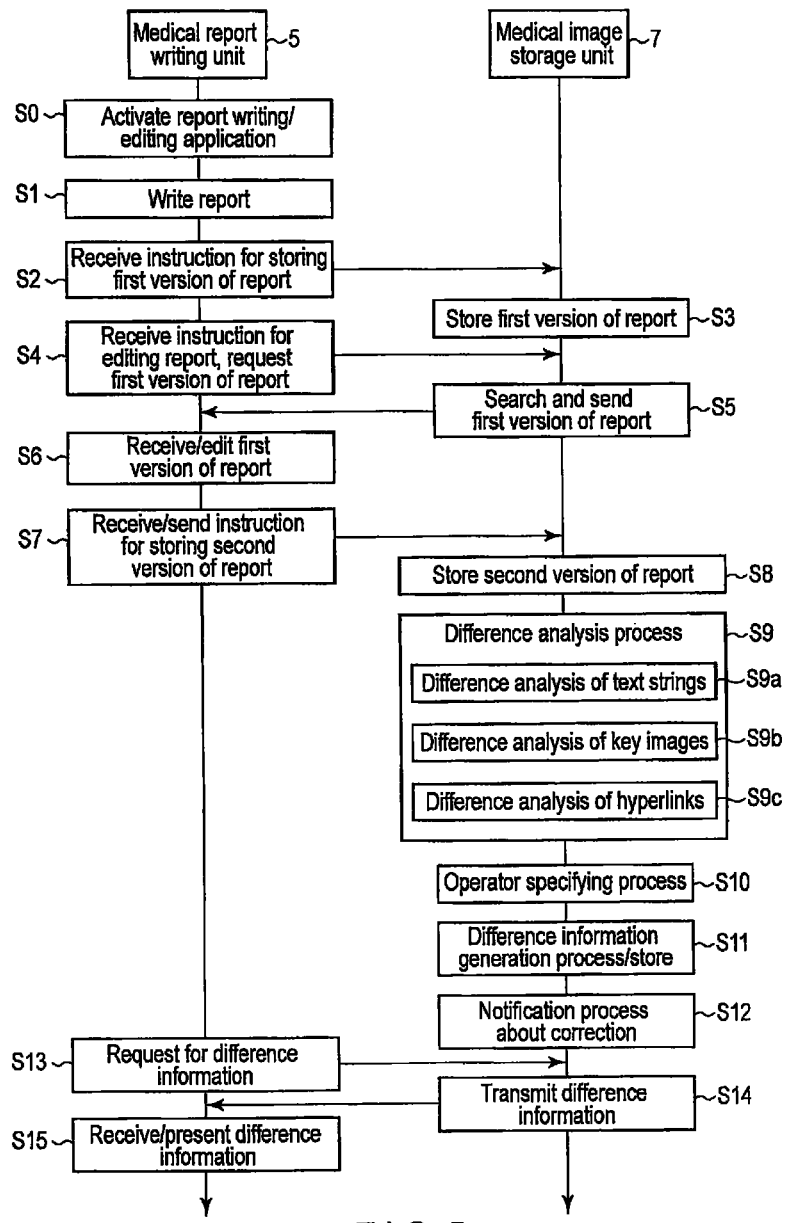
FIG. 5 is a flowchart illustrating the flow of a process (medical report writing support process) in accordance with a medical report writing support system according to a first embodiment.

FIG. 5 is a flowchart showing the flow of a process (medical report writing support process) executed by the medical report writing support system. Descriptions will now be made to concrete contents of each process executed in the medical report writing support process, with the flowchart.

If the primary operator inputs an instruction for starting to write a first report through the operation unit 50, the report data processing unit 52 activates the report writing/editing application (Step S0). In this case, the primary operator implies a young radiologist who writes the first (primary) report regarding corresponding examination. The control unit 53 writes a medical report, in response to the instruction input from the primary operator through the operation unit 50 in accordance with the application (Step 1). In the operation for writing the medical report, for example, some text string including a doctor's observation and a comment are written, a key image is inserted (attached), a hyperlink for a predetermined image or information is executed.

Upon completion of the report writing operation, the primary operator inputs a storage instruction through the operation unit 50. The report data processing unit 52 decides the written report as a "first version of a report", in response to the storage instruction (for example, an explicit storage instruction or an instruction for closing a report file). Then, the unit 52 transmits the first version of the report to the medical image storage unit 7 through the network N (Step S2). Upon reception of the first version of the report through the transmission/reception unit 75, the control unit 74 of the medical image storage unit 1 stores the report in the report database (Step S3).

When the secondary operator inputs an instruction for starting to edit the first version of the report for a corresponding patient though the operation unit 50 at a predetermined timing, the report data processing unit 52 activates the report writing/editing application, and sends a request to the medical image storage unit 7 for the first version of the report for the corresponding patient, through the network N (Step S4). The secondary operator implies an expert radiologist who executes further editing on the "first version of the report" written by the primary operator and writes the second version of the report. The control unit 74 of the medical image storage unit 7 searches the report database 71 for the first version of the report for the corresponding patient, and transmits the read report to the medical report writing unit 5 through the network N (Step S5).

Upon reception of the first version of the report from the medical image storage unit 7 through the network N, the report data processing unit 52 of the medical report writing unit 5 executes an editing process for the first version of the report, in response to an instruction input from the second operator through the operation unit 50 (Step S6). In this editing operation for the medical report, a text string including a doctor's observation and a comment is added, changed, and deleted, a key image is deleted, added, and changed, an image processing method is changed, and a hyperlink for a predetermined image or information is added, deleted, and changed. When the editing process is completed, the secondary operator inputs a storage instruction through the operation unit 50. The report data processing unit 52 decides the report after the editing process for the first version of the report, as a second version of a report, in response to the storage instruction, and transmits the second version of the report to the medical image storage unit 7 through the network N (Step S7). Upon reception of the second version of the report through the transmission/reception unit 75, the control unit 74 of the medical image storage unit 1 stores the second version of the report in the report database 71 (Step S8).

Figures 6, 7:
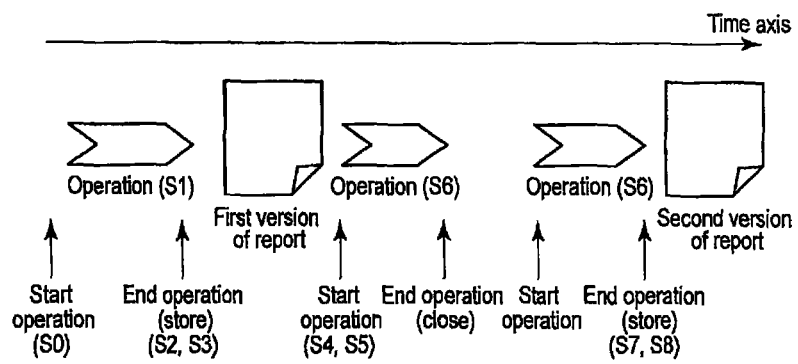
FIG. 6 is a diagram schematically illustrating the flow of each process from flowchart step S0 to step S8, showing a process (medical report writing support system) according to the first embodiment.
FIG. 7 is a diagram illustrating an example of difference notification, by displaying a "correction" mark on an examination list, after a participant operator logs into the medical report writing unit, according to the embodiment.

The flow of each of the above-described processes from Step S0 to S8 is conceptually illustrated in FIG. 6.

The difference information generation unit 73 of the medical image storage unit 7 executes a difference analysis process for a difference between the reports (Step S9). This difference analysis process is executed for the latest version of the report and a previous report therebefore (past report), as a trigger that the report for storage is received from the medical report writing unit 5. In this embodiment, the difference analysis process uses the first version of the report and the second version of the report.

That is, upon reception of the second version of the report for storage (that is, the latest medical report), the difference information generation unit 73 reads the first version of the report (that is, earlier version of the report) stored in the report database 71, compares the second version of the report and the first version of the report, and analyzes a difference between the two reports. This difference analysis can be classified as difference analysis of, for example, the text string, key image, or hyperlink. Descriptions will now be made to the contents of each analysis process.

(Step S9a: Difference Analysis of Text String)

The difference analysis generation unit 73 determines a difference between text strings included in the first version of the report and text strings included in the second version of the report, determines any text string (that is, text added into the first version of the report before editing) which exists in the second version of the report and does not exist in the first version of the report, and determines a text string (that is, text deleted from the first version of the report before editing) which exists in the first version of the report and does not exist in the second version of the report. When two symbol strings are given, a known algorithm for extracting a difference between the symbol strings may be applied. This algorithm is given for obtaining the "Shortest Edit Script" for converting one of the two symbol strings into the other.

(Step S9b: Difference Analysis of Key Images)

The difference information generation unit 73 determines a difference between a key image included in the first version of the report and a key image included in the second version of the report, determines a key image (a key image added into the first version of the report before editing) which exists in the second version of the report but does not exist in the first version of the report, and determines a key image (a key image deleted from the first version of the report before editing) which exists in the first version of the report but does not exist in the second version of the report. In the determination of the difference between the key images, a determination is also made as to whether a change is made to an image processing method (gradation change, enlargement/reduction, annotation, measurement process) for a key image attached to the first version of the report.

The analysis on a difference between the key images is achieved by analyzing a group of two key images. Specifically, a process as will be described below is executed.

The group of key images is defined below, as a group of "Image" indicating an image and "P" indicating an image processing parameter for "Image".

Key image K=(Image, P)

A group "P" of image processing parameters is defined as below.

The group of image processing parameters P={ p_k|k= 1 ... x}

Each "p_x" represents a set of an image processing type and a value, and is information of, for example, P_1={ "magnifying percentage=75%", "rotation=25°"} .

Further, a group of key images "I" is defined as below.

A group of key images I={ (Image_i, P_j)|i=1 ... y, j= 1 ... z}

At this time, two groups of key images "I" (group of key images in the first version of the report) and "I'" (group of key images in the second version of the report) are analyzed in accordance with the following standards (1) to (5).

(1) No difference is made between key images, if I=I'.
(2) (Image_i, P_j) is a key image without being edited, if (Image_i, P_j) included in "I" is included also in "I'".
(3) (Image_i, P_j) is a key image which has been deleted from "I", if "Image_i" included in "I" is not included in "I'".
(4) (Image_i, P_j) is a key image which has been added into "I", if "Image_i" included in "I'" is not included in "I".
(5) "Image_i" is a key image with a changed image processing method, if "Image_i" included in "I" is included in "I'", and if different "P_j" is combined with "Image_i".

In the above example, the key image is defined as having a set of an image and an image processing parameter, but may be defined as having only an image(s). In this case, a difference between key images includes only adding or deleting of a key image (that is, a change in the image processing method or image processing parameter is not assumed as a difference between key images).

(Step S9c: Difference of Hyperlinks)

A difference of hyperlinks specifies an added hyperlink to the report before editing, a deleted hyperlink from the report before editing, replacement of an image for a hyperlink in the report before editing, and whether there is a change in the hyperlinked text string to the image in the report before editing.

The hyperlink is defined as a set (URI, STRING) of a text string "STRING" with an attached hyperlink and an identifier "URI" specifying a destination hyperlink. At this time, a group of hyperlinks "L" in the first version of the report and a group of hyperlinks "L'" of the second version of the report are defined as below.

The group "L" of hyperlinks in the first version of the report={ (URI_i, STRING_j|i=1 ... s, j=1 ... t}

The group "L'" of hyperlinks in the second version of the report={ (URI'_k, STRING'_l)|k=1 ... x, l=1 ... y}

The analysis is made on each of a hyperlink added into the first version of the report, a deleted hyperlink, replacement of an image for a hyperlink, and a change in a hyperlinked text string, in accordance with the following standards (1) to (10).

(1) Check whether there is a hyperlink having the same text string as "STRING_n" in "L'", for a hyperlink (URI_m, STRING_n) included in "L".

(2) Set a hyperlink as "(URI'_m, STRING_n)" and check whether "URI_m" is the same as "URI'_m", if this hyperlink having the same text string as "STRING_n" exists in "L'".

(3) (URI_m, STRING_n)=(URI'_m, STRING_n), and there is no difference between the two hyperlinks, if "URI_m=URI'_m" in (2).

(4) (URI'_m, STRING_n) is a hyperlink corresponding to a replaced image for a hyperlink (URI_m, STRING_n) of the report before being edited, if "URI_m≠URI'_m" in (2).

(5) Check whether a hyperlink having the same "URI" as "URI_m" exists in "L'", for a hyperlink (URI_m, STRING_n) included in "L".

(6) Set a hyperlink as (URI_m, STRING'_n) and check whether "STRING_n" is the same as "STRING'_n", if this hyperlink having the same "URI" as "URI_m" exists in "L'".

(7) (URI_m, STRING_n)=(URI_m, STRING'_n), and there is no difference between the two hyperlinks, if "STRING_n=STRING'_n" in (6).
(8) (URI_m, STRING'_n) is a hyperlink with an edited hyperlink text string, for a hyperlink (URI_m, STRING_ n) of the report before being edited, if "STRING_n≠STRING'_n" in (6).
(9) Of hyperlinks included in "L'", a hyperlink without matching with any of the above checks (1) and (5) is assumed as a hyperlink which has been added into the report before edited.
(10) Of hyperlinks included in "L", a hyperlink whose matching hyperlink is not existed in "L'" in accordance with any of the checks (1) and (5) is assumed as a hyperlink which has been deleted from the report before being edited.

In the hyperlink, a plurality of images may be linked to one text string. At this time, the definition of the hyperlink is extended as will be described below, thereby extending the previous algorithm, adding and deleting an image to and from a hyperlink.
(URI_SET, STRING)
  URI_SET={ URI_i|i=1 ... x}

The difference information generation unit 73 executes an operator specifying process for each of the first version of the report and the second version of the report (Step S10). The operator specifying process is to specify an operator participated in writing a medical report of a particular version. A group "W" of operators (participant operators) participated in writing a particular medical report "d" of a particular version "e" is defined as below.

W={ operator i(i=1 to x) who notifies about completion of operation (editing or referring to a report) on a version before "e" of w_dei|d}

The difference information generation unit 73 specifies a participant operator who notifies about difference information, based on the group "W" of the participant operators.

The definition of the participant operators is not limited to the above. For example, the participant operator may not include all operators who notify about completion of operation, and may include only an operator who instructs for, for example, storage.

The difference information generation unit 73 generates difference information for showing to the participant operator about a difference between text strings, key images, and hyperlinks determined through the difference analysis process, and stores the generated information as accompanying information of the second version of the report in the report database 71 (Step S11). This difference information is generated in a form to recognize, for example, a difference of the second version of the report from the first version of the report, as will be described later. A specific form of the difference information will be described together with the contents of Step S15.

The difference information generation unit 73 generates information (notification of correction) for notifying the participant operator about existence of report difference information, and transmits the information to the medical report writing unit 5 (Step S12). This transmission of notification is performed as a trigger that, for example, difference information is generated. FIG. 7 shows a display example of notification of correction in a form of a correction mark on an examination list. This display is made after the participant operator logs into the medical report writing unit 7.

After the participant operator logs into the medical report writing unit 5, a request instruction for difference information is transmitted to the medical image storage unit 7 at an arbitrary timing, upon reception of an instruction from the participant operator confirming the notification of correction (Step S13). Upon reception of this request, the medical image storage unit 7 searches the report database 71 for the second version of the report, and transmits the report to the medical report writing unit 5 through the network N (Step S14).

The report data processing unit 52 of the medical report wiring unit 5 receives the second version of the report from the medical image storage unit 7 through the network 7, and presents difference information stored as accompanying information of the second version of the report in a predetermined form (Step S15). Descriptions will now be made to a specific example of the form for presenting the information.
(Presenting Form of Change in Text Strings)

Presenting (displaying) of a change in the text string includes displaying a change, including text added into the report before being edited or deleted text therefrom. As a result of the difference analysis process, a difference shown in FIG. 8 is displayed. In this illustration, a text string with strike-through has been deleted from the report before being edited. Any text string displayed in red is added into the report before being edited.

FIG. 8 shows an example in which strike-through is made in the unit of character (letter) text. However, not limited to this example, the strike-through may be made in the unit of words or characters. For example, if the strike-through is made in the unit of, for example, sentences, a difference in text strings is displayed as illustrated in FIG. 9.

The difference in text strings illustrated in FIG. 8 and FIG. 9 can be displayed in a form shown in FIG. 10, in the display unit 51 of the medical report writing unit 5.
(Change in Key Images)

The display of a change in key images distinguishably specifies an added key image, a deleted key image, and whether the key image before being edited has been edited (gradation change or enlargement/reduction), all for the first version of the report before being edited.

Figure 11:
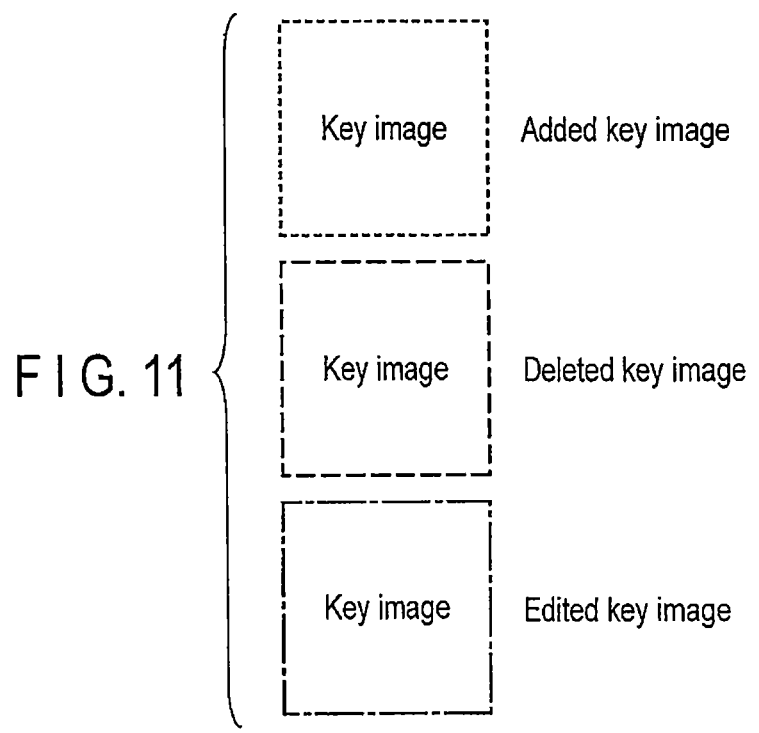
FIG. 11 is a diagram illustrating an example of a form showing a change in key images, according to the embodiment.
Figure 12:
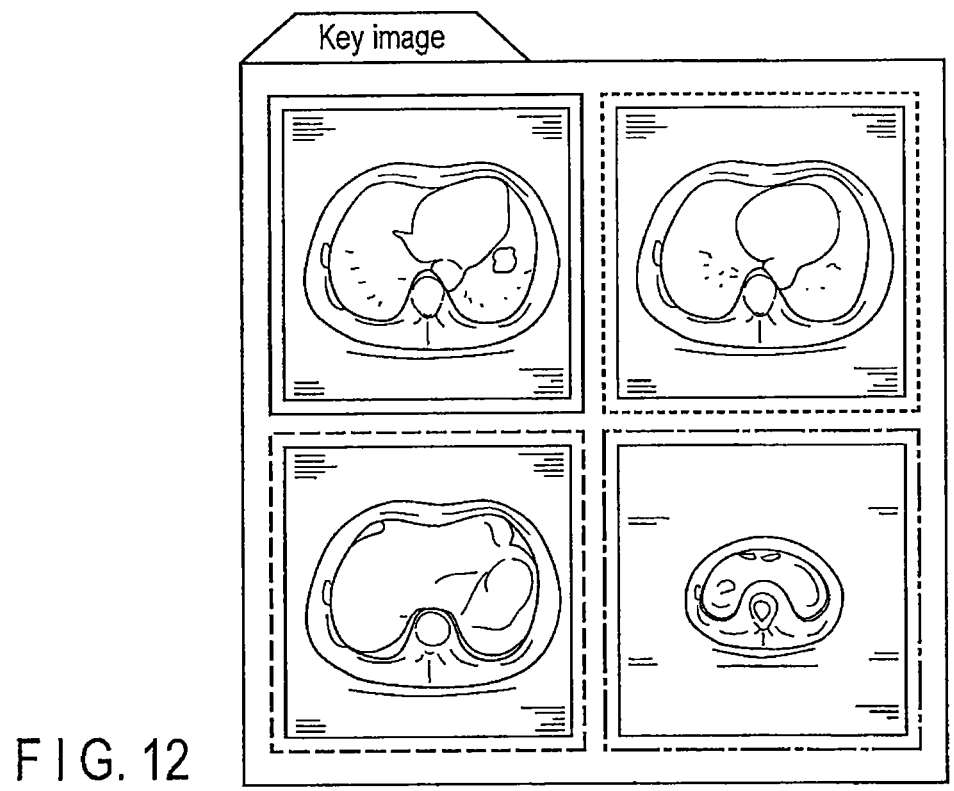
FIG. 12 is a diagram illustrating an example of a screen of a display unit showing a change in key images.

FIG. 11 and FIG. 12 are diagrams each showing an example of a form for presenting a change in key images. In the example of illustration, the type of frame of each image is distinguished, thereby distinguishing between an image without editing (displayed image has not been edited), an added image (image added to the first version of the report), a deleted image (image deleted from the first report), and an edited image (image with a changed parameter). Needless to say, the images may be distinguished therebetween based on not only the type of frame of each image, but also a frame color or predetermined mark. In the edited image, the image before editing and the image after edited may be arranged in a row, for example.
(Change in Hyperlinks)

The display of a difference between hyperlinks distinguishably specifies an added hyperlink, a deleted hyperlink, replacement of an image for a hyperlink, and a change in hyperlinked text strings (a text string with an allotted hyperlink), all for the first version of the report before being edited.

Figure 13:
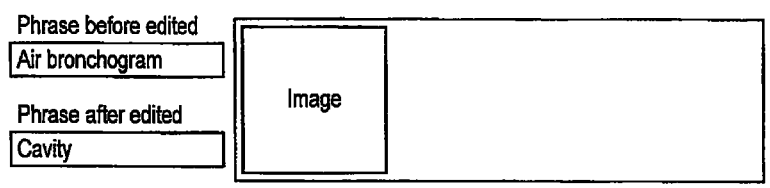
FIG. 13 is a diagram illustrating an example of a form showing a change in hyperlinks, according to the embodiment.

FIG. 13 illustrates a case in which the same hyperlinked image is provided for the first and second versions of the reports, and different hyperlinked text strings are provided. The example of this illustration specifies, as a change in hyperlinks, execution of a process for editing and changing a text string "air bronchogram" to a text string "cavity" hyperlinked thereto. These text strings are hyperlinked to an image 1.

Figure 14:
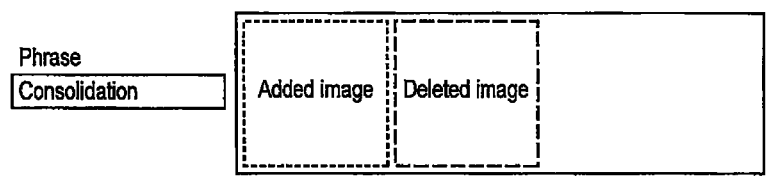
FIG. 14 is a diagram illustrating an example of a form showing a change in hyperlinks, according to the embodiment.

FIG. 14 shows an example of a case in which the same hyperlinked text image is provided and different hyperlinked images are provided. The example of this illustration specifies, as a change in hyperlinks, execution of an editing process for changing (replacing) "image 2" to "image 3" as a target hyperlink of the text string "consolidation". In FIG. 14, like FIG. 11 and FIG. 12, the types of frame of the image are distinguished, thereby distinguishing between an image without being edited, an added image, a deleted image, and an edited image.

Figure 15:
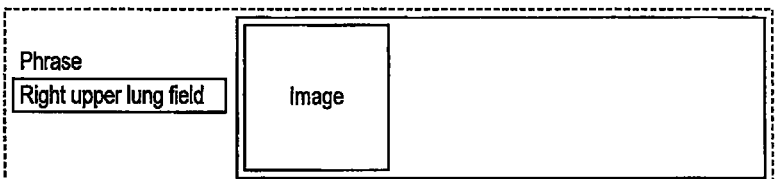
FIG. 15 is a diagram illustrating an example of a form showing a change in hyperlinks, according to the embodiment.

FIG. 15 is a diagram for explaining a change in hyperlinks, when a hyperlink is added or deleted. The example of this illustration shows, as a change in hyperlinks, the frame of an image 4 in blue. This blue display implies allotment of a new hyperlink for the image 4, for a text string "right upper lung field". If the hyperlink to the image 4 allotted to the text string "right upper lung field" is deleted, the frame of the image 4 is displayed in red, thereby specifying a change in the hyperlinks.

Figure 16:
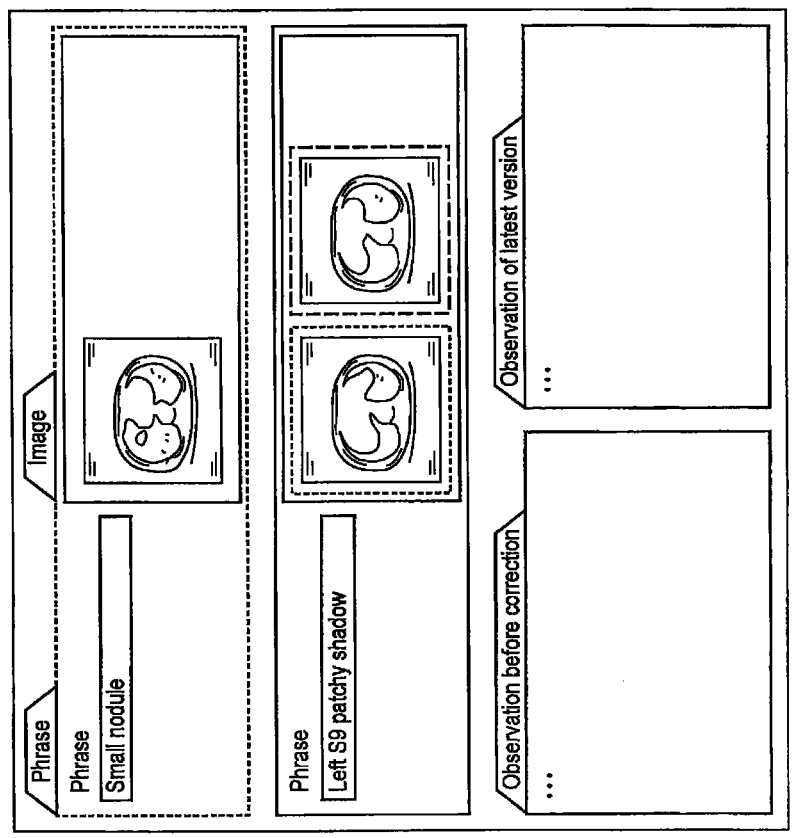
FIG. 16 is a diagram illustrating an example of a screen of a display unit showing a change in hyperlinks.

The change in the hyperlinks illustrated in FIGS. 13, 14, and 15 can be displayed in the form illustrated, for example, in FIG. 16, on the display unit 51 of the medical report writing unit 5.

(Effect)

According to the medical report writing support system of this embodiment, when a plurality of operators write and edit a medical report, an analysis is made on a difference between a predetermined report and a report with a version number smaller (old in time) than that of the predetermined report, and difference information is generated to certainly and clearly notify the operators about it. Specifically, an analysis is made on a medical report written through an editing process by the secondary operator and on a medical report written by the primary operator, when the expert radiologist as the second operator edits the contents of the temporarily stored report written by the young radiologist as the primary operator. As a result of the analysis, if there is a difference between the two medical reports, difference information is generated and given to the participant operators. The participant operators observe the given difference information, thereby quickly and easily recognizing a change in the first version of the report. As a result, for example, the primary operator can use the given difference information for a future (radiological) interpretation, thus contributing to improvement of quality in the medical image diagnosis.

Second Embodiment

In the first embodiment, as one example, the difference analysis process is executed, in accordance with storage of the second version of the report as a trigger. In a medical report writing support system according to the second embodiment, the report data processing unit 52 of the medical report writing unit 5 has the function of the difference information generation unit 73, and dynamically executes a difference analysis process at an arbitrary timing in which the operator intends to see a difference between the second version of the report and the first version of the report.

Figure 17:
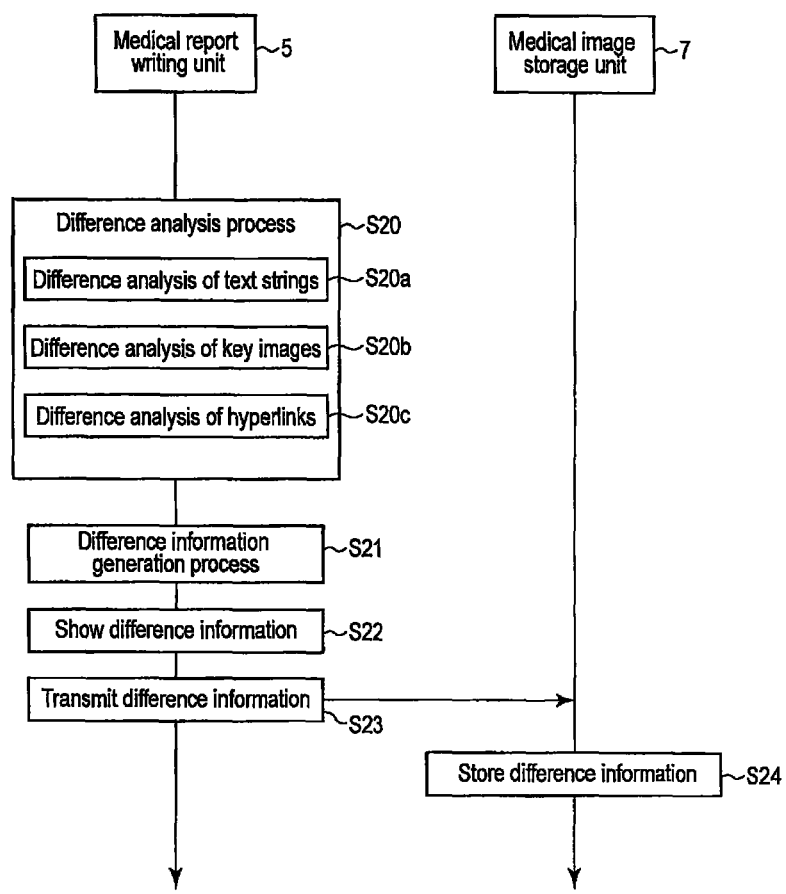
FIG. 17 is a flowchart illustrating the flow of a medical report writing support process, according to a second embodiment of the present invention.

FIG. 17 is a flowchart showing the flow of a medical report writing support process according to the second embodiment. In a typical case in which this flowchart is applied, a secondary operator intends to see a difference between the first version of the report and the second version of the report, when the secondary operator (or tertiary or higher operator) observes the second version of the report using the medical report writing unit 5.

As illustrated in FIG. 17, when execution of the medical report writing support process is input through the operation unit 50 at an arbitrary timing during the observation of the second version of the report, the report data writing unit 52 executes the same difference analysis process as that of Step S9 illustrated in FIG. 5 (Step S20).

The difference information generation unit 73 generates difference information for showing a difference between text strings, key images, and hyperlinks that are determined through the difference analysis process, to the participant operators (Step S21), and shows the difference information in the form shown in Step S15 (Step S22). The secondary operator observes the presented difference information, thereby visibly and easily recognizing a difference between the first version of the report and the second version of the report.

When it is intended to store the shown difference information, a predetermined instruction is input from the operation unit 50, the second version of the report having the difference information as accompanying information is transmitted to the medical image storage unit 7 through the network 7 (Step S23). The control unit 74 stores the second version of the report having the difference information as the accompanying information, in the report database 71 (Step S24).

According to the configuration described above, the medical report writing process according to the first embodiment can flexibly be executed.

The configuration may further include a comparison/verification unit which compares and verifies difference information (first difference information) stored as accompanying information of the second version of the report in Step S24, with difference information (second difference information) between the first version of the report and the second version of the report. This second difference information is newly generated at an arbitrary timing, after the first difference information is generated and stored. This configuration certainly realizes detection and notification about a fact in which any of the reports is rewritten by an unauthorized someone.

It is assumed, for example, after the first version and second version of the reports are stored in Step S24, a malicious third party may update any of the first and second versions of reports at an arbitrary timing. In this case, a difference is made between the first difference information and the second difference information, and the maliciously rewritten report and the difference information are updated and would be new data. Thus, when it is not understood about any of the reports has maliciously been rewritten, a problem is that the maliciously-rewritten report or difference information may be used.

The comparison/verification unit generates difference information for verification between the first version of the report and the second version of the report at an arbitrary timing. The comparison/verification unit compares the generated difference information for verification and the latest difference information of the stored difference information, and verifies whether there is a difference between the two. The medical report writing support system can inform the operator that the report has been updated by a third party, based on the difference detected by the comparison/verification unit. The above-described comparison/verification operation may be performed upon reception of a request for reading a report, or may be performed on the side of the unit at a predetermined timing (for example, regularly).

With this function, the falsified medical data can be detected, thus improving data reliability.

Third Embodiment

In the first and second embodiments, the difference information is stored in the report database 71 as accompanying information of the second version of the report. This difference information represents the text strings, the key images, and the hyperlinks, and is determined by the difference analysis process of the difference information generation unit 73. However, this difference information is not necessarily stored. Every time the operator requests for difference information, the difference information may be analyzed and shown to the operator. After this, this information may be destroyed without being stored.

Fourth Embodiment

According to the configuration of the first to third embodiments, difference information between the first version of the report and the second version of the report is always generated, based on the analyzed result. In the fourth embodiment, however, generation of the difference information is arbitrary, and a determination is made as to whether a difference exists between the first version of the report and the second version of the report based on the analyzed result. When determined that a difference exists between the two reports, the difference is actively given to the operators.

Figure 18:
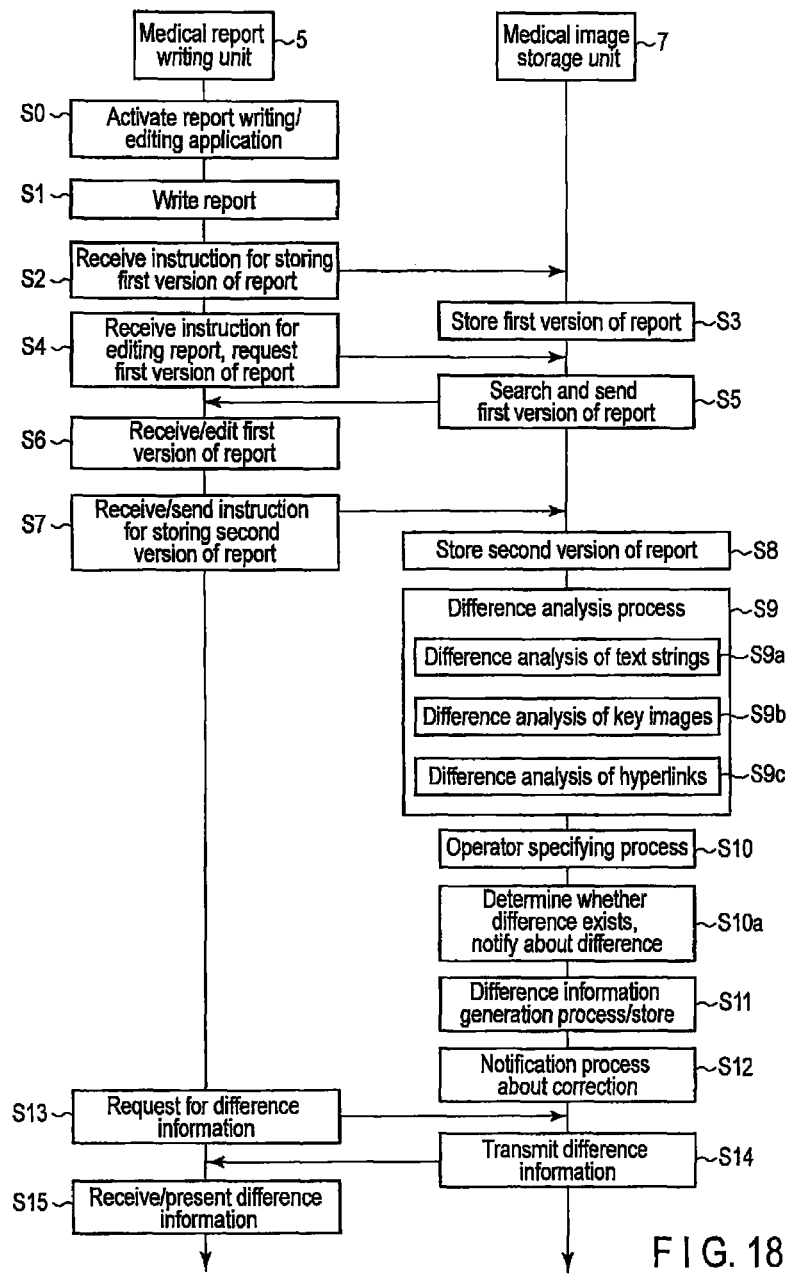
FIG. 18 is a flowchart showing an example of the flow of a medical report writing support process according to the fourth embodiment.

FIG. 18 is a flowchart showing an example of the flow of a medical report writing support process according to the fourth embodiment. When compared this illustration with FIG. 5, a difference is that Step S10a is newly added. That is, in each of Steps S0 to S10, the same contents described in the first embodiment are executed in each process. The difference information generation unit 73 determines whether a difference exists between the first version of the report and the second version of the report, based on a result of the difference analysis process. When it is determined that a difference exists, information about this difference is transmitted to the operator specified in Step S10 (that is, the medical report writing unit used by the corresponding operator to write the report), through the network (Step S10a).

After this information is transmitted, each process from Step S11 to S15 is executed like the first embodiment, and this medical report writing support process is completed.

FIG. 18 shows an example of a case for generating difference information. However, according to a configuration of this embodiment, information representing existence of the difference may actively be transmitted to the operator, without generating the difference information.

According to the above-described configuration, when a plurality of operators write and edit a medical report, each operator can rapidly and easily know a fact that a difference (correction on the doctor's observation) exists between a predetermined report and a report with a smaller version (old in time) than that of the predetermined report. As a result, for example, a primary operator can use the transmitted difference information for a future interpretation as needed, and can contribute to improvement of quality in image diagnosis.

The above-described embodiments are not limited in this context. In the practical phase, constituent elements may be modified and realized without departing from their point. Specific modifications may be realized as follows:

(1) Each of the functions of the above-described embodiments (e.g., as set forth in the above-described units) can be realized by installing programs executing the processes on a computer, (e.g., a processor containing circuitry), such as workstation, and by developing the programs into a memory. At this time, a program (a non-transitory computer readable medium) for controlling a computer to execute the corresponding technique can be distributed in a way that the program is stored in a magnetic disc (floppy (registered trademark) disc, hard disc), optical disc (CD-ROM, DVD), or a semiconductor memory.

(2) The medical report writing support system according to each of the above-described embodiment is realized with the image database 70 provided in the medical image storage unit 7, the report database 71, and the difference information generation unit 73, for example. However, without limiting to the above-described embodiments, the medical report writing support system can be realized, by storing target image data and medical report data in, for example, the medical report writing unit 5 and the medical image observation unit 3, and by having a function of the difference information generation unit 73.

The embodiments of the present invention have been described. The embodiments have been presented by way of example, and are not intended to limit scope of the present invention. These embodiments can be implemented in other forms, and can be omitted, replaced, and changed without departing from the scope of the present invention. These embodiments and their modifications are included in the scope or point of the present invention, and included within the inventions set forth in the claims and equivalent scope thereof.

The invention claimed is:

1. A medical report writing support system comprising
an analyzing unit which analyzes a difference regarding at least one of a change in a key image between a first report and a second report regarding a predetermined patient and a change in hyperlinks related to the key image, and acquires an analyzed result; and
a difference information generation unit which generates difference information based on the analyzed result, the difference information representing deletion or replacement of a key image attached to the first report, attachment of a new key image to the first report, change of an image parameter for the key image attached to the first report, correction, addition, and deletion of a comment on the key image attached onto the first report,
wherein the analyzing unit and the difference information generation unit comprise at least one processor programmed with non-transitory computer readable media.

2. The medical report writing support system according to claim 1, wherein
the difference information generation unit generates difference information representing at least any one of correction, addition, and deletion of a text string included in the first report, as the difference information.

3. The medical report writing support system according to claim 1, wherein
the difference information generation unit generates differential information representing any one of correction, addition, and deletion of a hyperlink included in the first report.

4. The medical report writing support system according to claim 1, further comprising:
a specification unit which specifies at least one of an operator of the second report, an operator who referred to the second report, and an operator who referred to the first report; and
a notification unit which notifies the specified operator that the difference information exists, when the difference information is generated.

5. The medical report writing support system according to claim 1, wherein
a predetermined instruction is an instruction for storing the second report.

6. The medical report writing support system according to claim 1, wherein a predetermined instruction is an instruction for starting the analysis, and is input at an arbitrary timing by an operator through an input unit.

7. A medical report writing support system comprising:
an analyzing unit which analyzes a difference regarding at least one of a change in a key image between a first report and a second report regarding a predetermined patient and a change in hyperlinks related to the key image, and determines whether a difference exists therebetween;
a specification unit which specifies at least one of an operator of the second report, an operator who referred to the second report, and an operator who referred to the first report;
a notification unit which notifies the specified operator about existence of the difference, when the analyzing unit determines that the difference exists; and
a difference information generation unit which generates difference information based on an analyzed result of the analyzing unit, the difference information representing at least one of deletion or replacement of a key image attached to the first report, attachment of a new key image to the first report, change in an image parameter for the key image attached to the first report, correction, addition, and deletion of a comment on the key image attached to the first report,
wherein the analyzing unit, the specification unit, the notification unit, and the difference information generation unit comprise at least one processor programmed with non-transitory computer readable media.

8. The medical report writing support system according to claim 7, wherein
the difference information generation unit generates differential information representing any one of correction, addition, and deletion of a hyperlink included in the first report.

9. The medical report writing support system according to claim 7, wherein
a predetermined instruction is an instruction for storing the second report.

10. The medical report writing support system according to claim 7, further comprising:
a specification unit which specifies at least one of an operator of the second report, an operator who has referred to the second report, and an operator who has referred to the first report; and
a notification unit which notifies the specified operator about existence of the difference information, when the difference information has been generated.

11. The medical report writing support system according to claim 7, wherein
a predetermined instruction is an instruction for starting the analysis and input by the operator through an input unit at an arbitrary timing.

12. A medical report writing unit comprising:
an analyzing unit which analyzes a difference regarding at least one of a change in a key image between a first version of a report and a second version of the report regarding a predetermined patient and a change in hyperlinks related to the key image, and acquires an analyzed result; and
a difference information generation unit which generates difference information based on the analyzed result, the difference information representing deletion or replacement of a key image attached to the first version of the report, attachment of a new key image to the first version of the report, change of an image parameter for the key image attached to the first version of the report, correction, addition, and deletion of a comment on the key image attached onto the first version of the report,
wherein the analyzing unit and the difference information generation unit comprise at least one processor programmed with non-transitory computer readable media.

13. A medical image observation unit comprising:
an analyzing unit which analyzes a difference regarding at least one of a change in a key image between a first version of a report and a second version of the report regarding a predetermined patient, and acquires an analyzed result; and
a difference information generation unit which generates difference information based on the analyzed result, the difference information representing deletion or replacement of a key image attached to the first version of the report, attachment of a new key image to the first version of the report, change of an image parameter for the key image attached to the first version of the report, correction, addition, and deletion of a comment on the key image attached onto the first version of the report,
wherein the analyzing unit and the difference information generation unit comprise at least one processor programmed with non-transitory computer readable media.

14. A medical report writing support system comprising:
an analyzing unit which analyzes a difference regarding at least one of a change in a key image between a first version of a report and a second version of the report regarding a predetermined patient and a change in hyperlinks related to the key image, and determines whether a difference exists therebetween;
a specification unit which specifies at least one of an operator of the second version of the report, an operator who has referred to the second version of the report, and an operator who has referred to the first version of the report;
a notification unit which notifies the specified operator about existence of the difference, when the analyzing unit determines that the difference exists; and
a difference information generation unit which generates difference information based on an analyzed result of the analyzing unit, the difference information representing at least one of deletion or replacement of a key image attached to the first version of the report, attachment of a new key image to the first version of the report, change in an image parameter for the key image attached to the first version of the report, correction, addition, and deletion of a comment on the key image attached to the first version of the report,
wherein the analyzing unit, the specification unit, the notification unit, and the difference information generation unit comprise at least one processor programmed with non-transitory computer readable media.

15. A medical image observation unit comprising:
an analyzing unit which analyzes a difference regarding at least one of a change in a key image between a first version of a report and a second version of the report corresponding to a predetermined patient and a change in hyperlinks related to the key image, and determines whether a difference exists therebetween;
a specification unit which specifies at least one of an operator of the second version of the report, an operator who has referred to the second version of the report, and an operator who has referred to the first version of the report;
a notification unit which notifies the specified operator about existence of the difference, when the analyzing unit determines that the difference exists; and a difference information generation unit which generates difference information based on an analyzed result of the analyzing unit, the difference information representing at least one of deletion or replacement of a key image attached to the first version of the report, attachment of a new key image to the first version of the report, change in an image parameter for the key image attached to the first version of the report, correction, addition, and deletion of a comment on the key image attached to the first version of the report, wherein the analyzing unit, the specification unit, the notification unit, and the difference information generation unit comprise at least one processor programmed with non-transitory computer readable media.

\* \* \* \* \*